(12) United States Patent
Suga

(10) Patent No.: US 7,241,274 B2
(45) Date of Patent: Jul. 10, 2007

(54) SANITARY TAMPON

(75) Inventor: Ayami Suga, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/038,863

(22) Filed: Jan. 18, 2005

(65) Prior Publication Data

US 2005/0171463 A1   Aug. 4, 2005

(30) Foreign Application Priority Data

Jan. 30, 2004   (JP) .............................. 2004-023644

(51) Int. Cl.
*A61F 13/20* (2006.01)

(52) U.S. Cl. .......................................... 604/15; 604/11

(58) Field of Classification Search ............. 604/11–15
See application file for complete search history.

(56) References Cited

U.S. PATENT DOCUMENTS 3,575,169 A * 4/1971 Voss et al. .................... 604/18
4,198,978 A * 4/1980 Nigro ........................... 604/14
4,447,222 A * 5/1984 Sartinoranont ............... 604/15
5,395,309 A * 3/1995 Tanaka et al. ................. 604/18
5,788,663 A * 8/1998 Igaue et al. ................... 604/15
6,190,348 B1 * 2/2001 Tiemann et al. .............. 604/15
7,081,110 B2 * 7/2006 Karapasha .................... 604/15
7,125,394 B2 * 10/2006 Berman et al. ................ 604/60

FOREIGN PATENT DOCUMENTS

| JP | 2000-279445 | 10/2000 |
|----|-------------|---------|
| JP | 2000-279446 | 10/2000 |

* cited by examiner

*Primary Examiner*—Tatyana Zalukaeva
*Assistant Examiner*—Ginger Chapman
(74) *Attorney, Agent, or Firm*—Darby & Darby

(57) ABSTRACT

Disclosed is a sanitary tampon including: an applicator composed of an outer tube having a front nose and a rear opening and a pusher inserted into the outer tube through the rear opening; and a tampon body contained in the outer tube and allowed to come out of the front nose when pushed by the pusher. The outer tube is provided with marks which serve as a measure of insertion distance of the outer tube into the vaginal cavity of a user. The marks are spaced away from the front nose of the outer tube.

6 Claims, 3 Drawing Sheets

SANITARY TAMPON

CROSS-REFERENCE TO RELATED APPLICATION

The application claims priority under 35 U.S.C. § 119 from Japanese Patent application No. 2004-23644, filed Jan. 30, 2004.

BACKGROUND OF THE INVENTION

1. Field of the Invention

The present invention relates to a sanitary tampon having a tampon body to be inserted into the vaginal cavity with an applicator.

2. Description of the Prior Art

Sanitary tampons are frequently used with applicators. Such applicators are generally composed of an outer tube made of synthetic resin and a pusher inserted into the outer tube through an opening formed at a rear end of the outer tube. At its front end, the outer tube has a nose formed with a plurality of deformable petal tips. A tampon body capable of absorbing and retaining liquid is contained in the outer tube. When using the sanitary tampon, the outer tube of the applicator is inserted into the vaginal cavity and the tampon body in the outer tube is pushed by the pusher to come out of the nose into the vaginal cavity.

Because a sphincter surrounds the vaginal opening, the tampon body will compress the sphincter to give a user an unpleasant feeling unless the tampon body is located in the deep part of the vaginal cavity beyond the sphincter.

Japanese Unexamined Patent Publication No. 2000-279445 discloses an applicator whose outer tube is sufficiently longer than a tampon body to have a rear portion which serves as a holding rod. Inserting the outer tube into the vaginal cavity with holding the holding rod enables the front end of the outer tube to reach the deep part of the vaginal cavity, so that the tampon body can be easily located in the deep part of the vaginal cavity beyond the sphincter.

Japanese Unexamined Patent Publication No. 2000-279446 discloses an applicator whose outer tube is provided with a largest outside diameter portion near the front end. The outside diameter of the outer tube increases gradually rearward from the front end and further gradually diminishes rearward after arriving at the largest outside diameter portion. In this invention, as the outer tube of the applicator is inserted into the vaginal cavity, the largest outside diameter portion of the outer tube easily reaches the deep part of the vaginal cavity after passing the sphincter around the vaginal opening. As a result, the tampon body can be easily located in the deep part of the vaginal cavity.

In both Japanese Unexamined Patent Publication Nos. 2000-279445 and 2000-279446, the outer tube is enabled to reach the deep part of the vaginal cavity, facilitating the deep insertion of the tampon body into the vaginal cavity.

However, these applicators may sometimes be inserted more deeply than necessary. It may also happen that the tampon body pushed out of the outer tube is located shallower than expected and in the vicinity of the vaginal opening surrounded by the sphincter, which results in compressing the sphincter to give a user an unpleasant feeling.

The depth of the vaginal cavity varies between individuals depending on the body height etc. The location and size of the sphincter also vary between individuals. In addition, they vary with the growth even for the same person. Accordingly, users are not uniform in suitable location of the tampon body in the vaginal cavity, and therefore, users are not uniform in suitable insertion distance of the applicator into the vaginal cavity, either.

SUMMARY OF THE INVENTION

It is an object of the present invention to provide a sanitary tampon which allows easy adjustment of insertion distance of an applicator into the vaginal cavity of a user.

According to a first aspect of the present invention, there is provided a sanitary tampon comprising:

an applicator composed of an outer tube having a front nose and a rear opening and a pusher inserted into the outer tube through the rear opening; and a tampon body contained in the outer tube and allowed to come out of the front nose when pushed by the pusher, the outer tube being provided with marks which serve as a measure of insertion distance of the outer tube into the vaginal cavity of a user, the marks being spaced away from the front nose of the outer tube.

With reference to the marks provided on the outer tube, the user can insert the outer tube into the vaginal cavity without feeling any anxiety until its front end reaches an appropriate depth.

Preferably the marks include a first mark indicating a minimum distance beyond which the outer tube should be inserted into the vaginal cavity. In other words, the first mark teaches that at least a portion forward of this mark should be inserted into the vaginal cavity. With this first mark, insufficient insertion of the outer tube can be prevented.

Also preferably the marks include a last mark indicating a maximum distance beyond which the outer tube should not be inserted into the vaginal cavity. In other words, the last mark warns that a portion rearward of this mark should not be inserted into the vaginal cavity. With this last mark, excessive insertion of the outer tube can be prevented.

Most preferably the marks include the first mark, the last mark, and optionally at least one intermediate mark between the first mark and the last mark. This intermediate mark may facilitate the user pinpointing the optimum location where insertion of the outer tube should be stopped. This optimum location varies between individuals.

In the present invention, the marks may be recognizable by touch and sight. In one preferred embodiment, the marks project from an exterior surface of the outer tube so as to be clearly perceived with the touch of a finger. More preferably the last mark is larger in projection height than the others as measured from the exterior surface of the outer tube. If the outer tube is accidentally inserted too deeply into the vaginal cavity, this last mark touches the mouth of the vagina to let the user recognize that further insertion is undesirable while the other marks give less resistance to the mouth of the vagina. In this embodiment, furthermore, one or more of the marks may be allowed to be crushed down. Crushing down unnecessary marks to leave only one mark which indicates the optimum insertion distance for the user leads to precise insertion to the optimum depth.

In the present invention, an explanation of the marks may be given in at least either of an instruction for use or a packaging.

As described above, the marks provided on the outer tube as a measure of insertion distance enable the outer tube to be inserted to the optimum depth without anxiety, which results in easy positioning of the tampon body in the vaginal cavity.

According to a second aspect of the present invention, there is provided a sanitary tampon comprising:

an applicator composed of an outer tube having a front nose and a rear opening and a pusher inserted into the outer tube through the rear opening; and a tampon body contained in the outer tube and allowed to come out of the front nose when pushed by the pusher, the outer tube being provided with a mark which serves as a measure of insertion distance of the outer tube into the vaginal cavity of a user, the mark being spaced from the front nose of the outer tube.

This mark may indicate a minimum distance beyond which the outer tube should be inserted into the vaginal cavity or a maximum distance beyond which the outer tube should not be inserted into the vaginal cavity.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
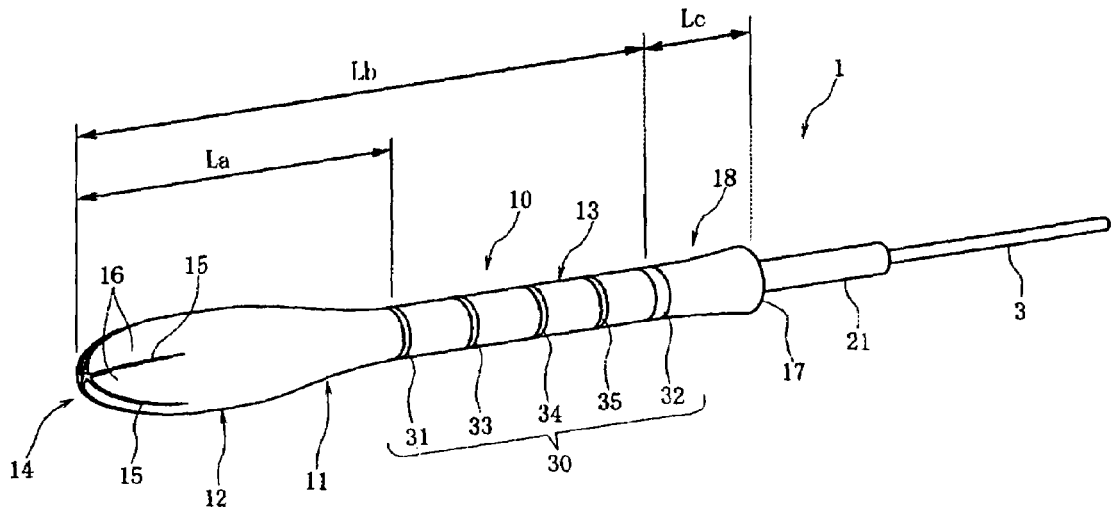
FIG. 1 is a perspective view of a sanitary tampon according to a first embodiment of the invention.

FIG. 1 shows a sanitary tampon 1 according to a first embodiment of the present invention. The sanitary tampon 1 has a tampon body 2 and an applicator 10 housing the tampon body 2.

The tampon body 2 may be formed by compressing absorbent fibers such as cotton and rayon. To the rear end of the tampon body 2, a withdrawal string 3 is connected. The tampon body 2 has a length L2 of about 20 to 60 mm. If the length L2 is less than 20 mm, the ability to absorb menstrual blood within the vaginal cavity may possibly degrade to an insufficient level. If the length L2 is greater than 60 mm, on the other hand, the rear portion of the tampon body 2 may possibly compress a sphincter around the mouth of the vaginal cavity to give a user an unpleasant feeling even if the tampon body 2 is located in the deep part of the vaginal cavity beyond the sphincter.

The applicator 10 has an outer tube 11 which may be made of thermoplastic resin such as PE (polyethylene) or PP (polypropylene) by injection molding process. The outer tube 11 has a head (or large-diameter portion) 12 on its front side. In this head 12, the diameter of the outer tube increases gradually rearward from the front end and further gradually diminishes rearward after arriving at the largest diameter portion. Rearward of the head 12, the outer tube has a tail (or small-diameter portion) 13 which is much smaller in diameter than the head 12. The boundary between the head 12 and the tail 13 is located forward of the midpoint of the length L1 of the outer tube 11.

At the front end of the outer tube 11, i.e., at the front end of the head 12, there is provided a front nose 14. The front nose 14 refers to a portion where a plurality of slits 15 extend a given distance rearward from the front end of the outer tube 11 to provide a plurality of petal tips 16. As shown in FIG. 1, each petal tip 16 defined between adjacent slits 15 gradually decreases in width toward the front end of the outer tube 11. When the tampon body 2 in the outer tube 11 is pushed forward to come out of the front nose 14, these petal tips 16 are deformed to open the front nose 14.

Near the rear end of the outer tube 11, the tail 13 slightly increases in diameter rearward. At the rear end of the outer tube 11, moreover, a rear opening 17 is formed to lead inside the outer tube 11. The applicator 10 also has a pusher (or inner tube) 21 inserted into the outer tube 11 through the rear opening 17.

The pusher 21 may be made of thermoplastic resin such as PE, PP or PET (polyethylene terephthalate) by injection molding process. At its front end, the pusher 21 is slightly increased in diameter to have an abutment 22, as shown in FIG. 2.

The length L1 of the outer tube 11 is sufficiently larger than the length L2 of the tampon body 2. The length L1 is such that even after the head 12 is deeply inserted into the vaginal cavity, a rear portion of the tail 13 can always stay outside the vagina. The length L1 is preferably in the range of 80 to 140 mm.

Figure 2:
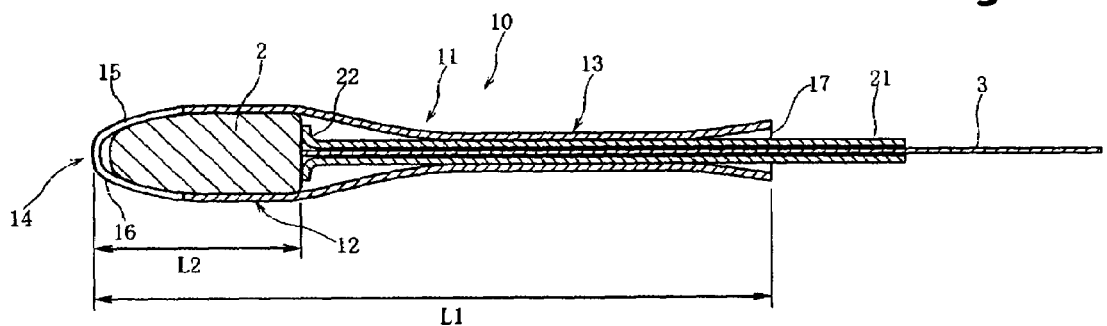
FIG. 2 is a sectional view of the sanitary tampon of FIG. 1.

As shown in FIG. 2, the tampon body 2 is housed in the head 12 and the withdrawal string 3 connected to the tampon body 2 passes through the interior space of the pusher 21 and extends outward from the rear end of the pusher 21.

On the interior surface of the outer tube 11, as shown in FIG. 1, there are provided marks 30 which serve as a measure of insertion distance of the outer tube 11 into the vaginal cavity. The marks 30 include a first mark 31 spaced a distance La rearward from the front end of the outer tube 11 and a last mark 32 spaced a distance Lb rearward from the front end of the outer tube 11. The marks 30 also include intermediate marks (or second, third and fourth marks) 33, 34 and 35 which divide the distance between the first mark 31 and the last mark 32 into equal parts.

When a user inserts the outer tube 11 into the vaginal cavity, any one of the marks 30 may be used as a benchmark for measurement of insertion distance of the outer tube 11 into the vaginal cavity. The user may choose any one of the marks 30 depending on the depth of the vaginal cavity, the location of the sphincter, etc. which vary between individuals.

The first mark 31 indicates a minimum distance beyond which the outer tube 11 should be inserted into the vaginal cavity for average adult women. The distance La measured from the front end of the outer tube 11 is equal to or greater than 40 mm, preferably in the range of 50±10 mm. If the distance La is less than 40 mm and the insertion distance of the outer tube 11 into the vaginal cavity is equal to the distance La, the tampon body 2 pushed out of the front nose 14 may possibly be located not in the deep part of the vaginal cavity but close to the sphincter around the mouth of the vagina to give a user an unpleasant feeling.

The last mark 32 indicates a maximum distance beyond which the outer tube 11 should not be inserted into the vaginal cavity for average adult women. The distance Lb measured from the front end of the outer tube 11 is up to about 110 mm, preferably in the range of 70 to 110 mm.

Rearward of the last mark 32, the outer tube 11 has a knob 18 to be held by fingers. The knob 18 has a length Lc which is preferably equal to or greater than 10 mm.

The first mark 31, second mark 33, third mark 34, fourth mark 35 and last mark 32, i.e., the marks 30 are preferably arranged at a constant pitch. The pitch may be in the range of 5 to 10 mm.

Figure 3:
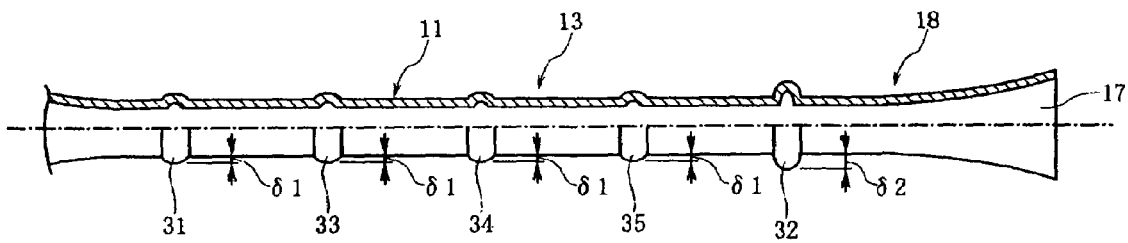
FIG. 3 is a half-sectional view of a tail of an outer tube used for the sanitary tampon of FIG. 1.

As shown in FIG. 3, the individual marks 31, 32, 33, 34, 35 project from the exterior surface of the outer tube 11 like a ring on the tail 13. In order not to give the vagina an unpleasant feeling, the first mark 31 and the intermediate marks 33, 34, 35 have a smooth, round surface as shown in FIG. 3. As measured from the exterior surface of the outer tube 11, the first mark 31 and the intermediate marks 33, 34, 35 have a projection height $\delta 1$ in the range of 0.1 to 0.5 mm so as to be perceived with the touch of a finger but not to give the vagina an unpleasant feeling during insertion.

Preferably the last mark 32 also has a smooth, round surface as shown in FIG. 3. As measured from the exterior surface of the outer tube 11, however, the last mark 32 has a projection height $\delta 2$ which is larger than the projection height $\delta 1$ and may be in the range of 1 to 5 mm. With the last mark 32 being raised higher than the others, the limit of insertion of the outer tube 11 into the vaginal cavity can be easily recognized.

When using the sanitary tampon 1, the applicator 10 is inserted into the vaginal cavity with the front nose 14 of the outer tube 11 being directed toward the vagina. Then the tampon body 2 is pushed by the pusher 21, whereby the petal tips 16 are deformed to open the front nose 14 of the outer tube 11 and the tampon body 2 comes out of the outer tube 11 into the vaginal cavity.

Even for a first-time user, it is easy to avoid inadequate or excessive insertion of the outer tube 11 into the vaginal cavity by referring to the first and last marks 31, 32. Especially, the last mark 32 eliminates the fear of excessive insertion into the vaginal cavity.

In addition, if a user knows which one of the marks 30 is suitable for use as a benchmark for measurement of insertion distance, she can always insert the outer tube 11 to an appropriate depth without difficulty. That is, once the appropriate insertion depth is found by a user after using the same sanitary tampons several times, insertion to the appropriate depth can be easily performed by referring to the benchmark.

For example, if the third mark 34 is found to be a suitable mark, the outer tube 11 is inserted into the vaginal cavity until her finger put on the third mark 34 reaches the mouth of the vagina. Then, the tampon body 2 is pushed out of the outer tube 11 by pushing the pusher 21 and left in an appropriate deep part of the vaginal cavity.

Figure 4:
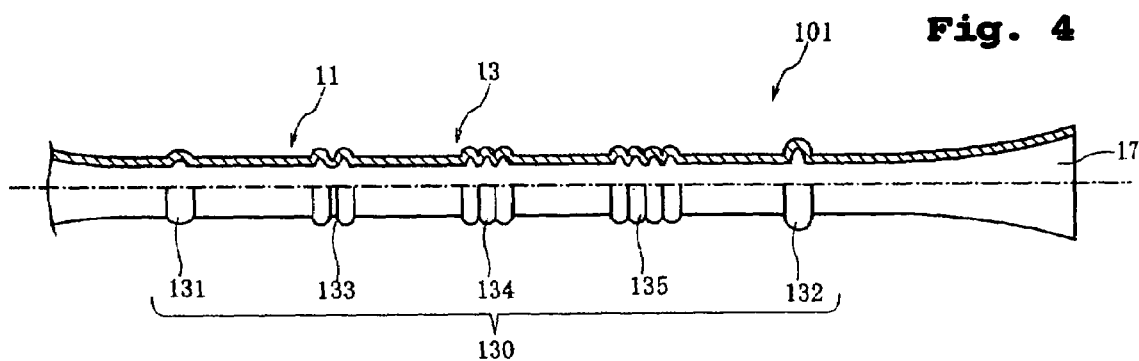
FIG. 4 is a half-sectional view of a tail of an outer tube used for a sanitary tampon according to a second embodiment of the invention.

FIG. 4 is a half-sectional view of the tail 13 of the outer tube 11 used for a sanitary tampon 101 according to a second embodiment of the invention. In this sanitary tampon 101, marks 130 are able to be distinguished from one another by touching them with a finger.

The outer tube 11 is integrally formed with the marks 130 each projecting like a ring. The marks 130 include: a first mark 131 of one ring-like projection; a second mark 133 of two ring-like projections; a third mark 134 of three ring-like projections; a fourth mark 135 of four ring-like projections; and a last mark 132 of one ring-like projection, wherein the first mark 131 and the intermediate marks 133, 134, 135 have the same projection height $\delta 1$ as the marks 31, 33, 34, 35 of FIG. 3, whereas the last mark 132 has the same projection height $\delta 2$ as the last mark 32 of FIG. 3.

In the second embodiment, the last mark 132 may be composed of five ring-like projections or more.

Figure 5:
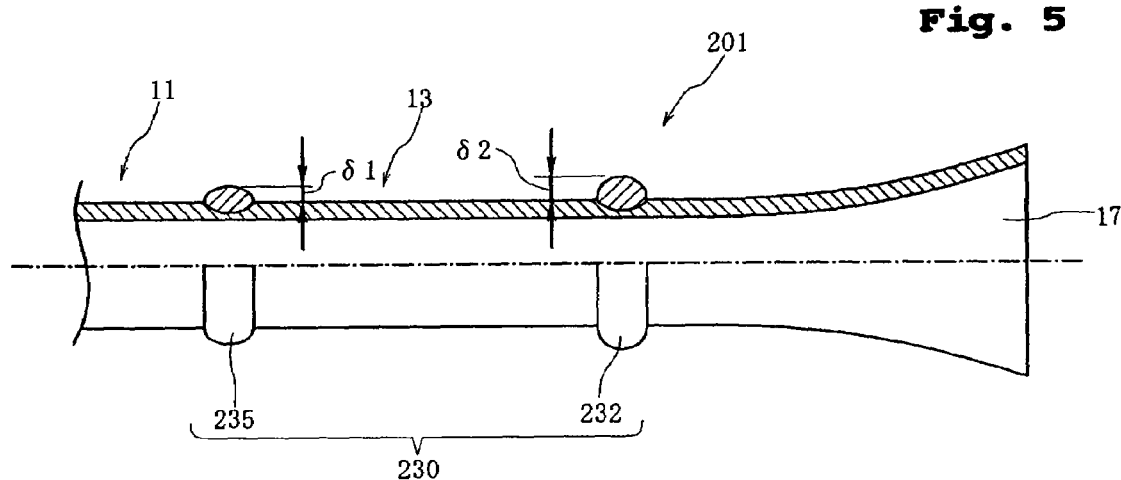
FIG. 5 is a half-sectional view of a tail of an outer tube used for a sanitary tampon according to a third embodiment of the invention.

FIG. 5 is a half-sectional view of the tail 13 of the outer tube 11 used for a sanitary tampon 201 according to a third embodiment of the invention.

Also in the third embodiment, five marks 230 are provided on the outer tube 11. It should be noted that FIG. 5 only shows fourth and last marks 235, 232, but omitted first, second and third marks are of the same shape and structure as the fourth mark 235. The marks 230 of the third embodiment are formed separate from the outer tube 11. More specifically, ring-like grooves are formed in the exterior surface of the outer tube 11 and another material is fitted in the grooves to form the marks 230. Preferably this material used for forming the marks 230 has no harmful effect on the human body and is more flexible than the synthetic resin used for forming the outer tube 11. For example, elastic members such as silicon rubber rings may be fitted in and bonded to the grooves so as not to cause displacement.

With such a flexible or elastic material, the marks 230 hardly give an unpleasant feeling to the vagina. In this embodiment, moreover, the last mark 232 has the projection height $\delta 2$ and the other marks have the projection height $\delta 1$. Also in this embodiment, the intermediate marks and optionally the last mark may be composed of two or more rings as shown in the lower half of FIG. 4.

Figure 6:
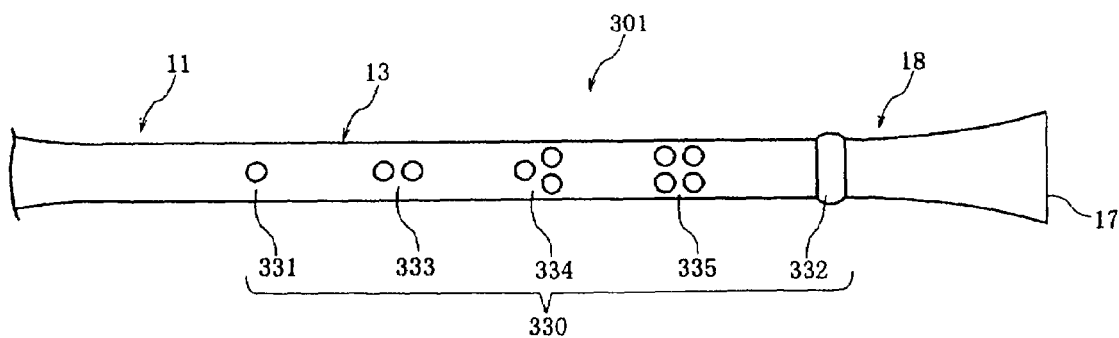
FIG. 6 is a side view of a tail of an outer tube used for a sanitary tampon according to a fourth embodiment of the invention.

FIG. 6 is a side view of the tail 13 of the outer tube 11 used for a sanitary tampon 301 according to a fourth embodiment of the invention.

The outer tube 11 is integrally formed with marks 330. The marks 330 include: a first mark 331 of one circular projection; a second mark 333 of two circular projections; a third mark 334 of three circular projections; a fourth mark 335 of four circular projections; and a last mark 332 of one ring-like projection. The last mark 332 is similar to the last mark 32 of FIG. 3 and the last mark 132 of FIG. 4. Also in this embodiment, the marks 330 are able to be distinguished from one another by touching them with a finger.

FIGS. 7(A) and 7(B) and FIGS. 8(A) and 8(B) are sectional views showing preferred structures of the circular projection of the first mark 331. The circular projections of the intermediate marks 333, 334, 335 are of the same structure as the circular projection of the first mark 331.

Figure 7A:
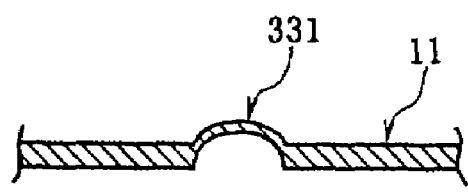
FIGS. 7(A) and 7(B) are sectional views showing a preferred structure of a circular projection of FIG. 6.
Figure 7B:
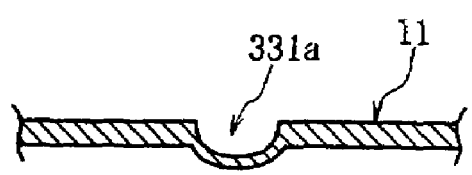
Figure 8A:
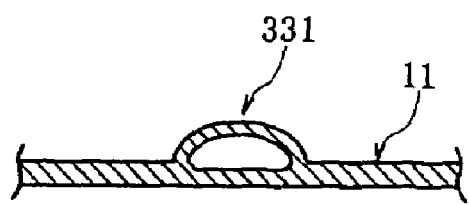
FIGS. 8(A) and 8(B) are sectional views showing a preferred structure of a circular projection of FIG. 6.

In FIG. 7(A), the circular projection of the first mark 331 is integral with the outer tube 11 but much thinner than the surrounding wall portion of the outer tube 11. The first mark 331 of FIG. 7(A) is allowed to be crushed down (or recessed) by a finger as indicated by 331a in FIG. 7(B). In an alternative, the circular projection of the first mark 331 may be formed as shown in FIG. 8(A). The first mark 331 of FIG. 8(A) is allowed to be crushed down (or flattened) by a finger as indicated by 331a in FIG. 8(B).

Figure 8B:
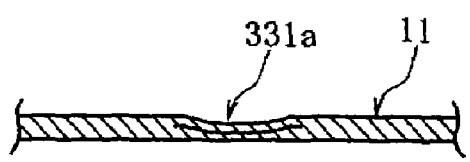

As described hereinabove, because the optimum insertion distance varies between individuals, a user may select one of the marks as a suitable benchmark. At this time, the user can easily recognize the selected mark by crushing down the other unnecessary marks as shown in FIG. 7(B) or 8(B). Moreover the crushed unnecessary marks become less recognizable also during insertion of the outer tube 11 into the vaginal cavity.

The sanitary tampon of the present invention may be embodied in various ways by combining the features of the foregoing embodiments.

In the foregoing embodiments, furthermore, the marks may be colored in different colors so as to be easily distinguished from one another by sight.

In the present invention, it is not necessarily required to provide projections on the tail 13 of the outer tube 11. Also in this case, the marks may be colored in different colors so as to be easily distinguished from one another by sight.

Also in the present invention, the number of marks may be arbitrarily increased or decreased. For example, the intermediate marks may be omitted to leave only the first and last marks. It is also possible to provide the outer tube with a single mark which indicates a minimum distance beyond which the outer tube should be inserted into the vaginal cavity or a maximum distance beyond which the outer tube should not be inserted into the vaginal cavity.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. A sanitary tampon comprising:
   an applicator composed of an outer tube having a front nose and a rear opening and a pusher inserted into the outer tube through the rear opening; and
   a tampon body contained in the outer tube and allowed to come out of the front nose when pushed by the pusher,
   the outer tube being provided with marks which serve as a measure of insertion distance of the outer tube into the vaginal cavity of a user, the marks being spaced away from the front nose of the outer tube, wherein
   the marks project from an exterior surface of the outer tube so as to be recognizable by touch and sight and include a first mark indicating a minimum distance beyond which the outer tube is insertable into the vaginal cavity and a last mark indicating a maximum distance beyond which the outer tube should not be inserted into the vaginal cavity,
   the first mark has a projection height of 0.1 to 0.5 mm as measured from the exterior surface of the outer tube, and
   the last mark has a larger projection height than the first mark as measured from the exterior surface of the outer tube and is located closer to the rear opening of the outer tube than the first mark.

2. A sanitary tampon according to claim 1, wherein the marks include at least one intermediate mark between the first mark and the last mark.

3. A sanitary tampon according to claim 2, wherein the intermediate mark has a projection height of 0.1 to 0.5 mm as measured from the exterior surface of the outer tube.

4. A sanitary tampon according to claim 1, wherein an explanation of the marks is given in at least either of an instruction for use or a packaging.

5. A sanitary tampon according to claim 1, wherein the last mark has a projection height of 1 to 5 mm as measured from the exterior surface of the outer tube.

6. A sanitary tampon comprising:
   an applicator composed of an outer tube having a front nose and a rear opening and a pusher inserted into the outer tube through the rear opening; and
   a tampon body contained in the outer tube and allowed to come out of the front nose when pushed by the pusher,
   the outer tube being provided with marks which serve as a measure of insertion distance of the outer tube into the vaginal cavity of a user, the marks being spaced away from the front nose of the outer tube,
   wherein the marks project from an exterior surface of the outer tube so as to be recognizable by touch and sight and include a last mark indicating a maximum distance beyond which the outer tube should not be inserted into the vaginal cavity and the last mark is larger in projection height than the others as measured from the exterior surface of the outer tube and is located closer to the rear opening of the outer tube than the others, and
   wherein the marks are formed integral with the outer tube, and a wall thickness of the outer tube is reduced in the marks so as to allow one or more of the marks to be crushed down.

* * * * *